(12) United States Patent
Van Kranenburg et al.

(10) Patent No.: US 8,663,954 B2
(45) Date of Patent: Mar. 4, 2014

(54) FERMENTATION OF MODERATELY THERMOPHILIC BACILLI ON SUCROSE

(75) Inventors: Richard Van Kranenburg, Wageningen (NL); Mariska Van Hartskamp, Gorinchem (NL)

(73) Assignee: Purac Biochem B.V., Gorinchem (NL)

( * ) Notice: Subject to any disclaimer, the term of this patent is extended or adjusted under 35 U.S.C. 154(b) by 0 days.

(21) Appl. No.: 13/384,527

(22) PCT Filed: Jul. 15, 2010

(86) PCT No.: PCT/EP2010/060220
§ 371 (c)(1),
(2), (4) Date: Mar. 22, 2012

(87) PCT Pub. No.: WO2011/006966
PCT Pub. Date: Jan. 20, 2011

(65) Prior Publication Data
US 2012/0208248 A1 Aug. 16, 2012

(30) Foreign Application Priority Data
Jul. 17, 2009 (EP) .................................. 09165828

(51) Int. Cl.
| | |
|---|---|
| *C12P 7/56* | (2006.01) |
| *C12P 7/40* | (2006.01) |
| *C12P 7/06* | (2006.01) |
| *C12P 7/26* | (2006.01) |
| *C12P 7/18* | (2006.01) |

(52) U.S. Cl.
USPC ........... 435/139; 435/136; 435/161; 435/148; 435/158

(58) Field of Classification Search
None
See application file for complete search history.

(56) References Cited

U.S. PATENT DOCUMENTS

2010/0112652 A1    5/2010   Bogaert

FOREIGN PATENT DOCUMENTS

| EP | 1953234 | 8/2008 |
|---|---|---|
| WO | WO 2004/063382 | 7/2004 |
| WO | WO 2007/085443 | 8/2007 |

OTHER PUBLICATIONS

Fouet et al., "*Bacillus subtilis* sucrose-specific enzyme II of the phosphotransferase system: Expression in *Escherichia coli* and homology to enzymes II from enteric bacteria", PNAS 84:8773-8777, 1987.*
GenBank Accession No. CAG25843, Apr. 2005, 2 pages.*
Kotay et al., Bioresource Technol. 98:1183-1190, 2007.*
Shukla et al., Biotechnol. Lett. 26:689-693, 2004.*
Schmid et al., J. Bacteriol. 151:68-76, 1982.*
GenBank Accession No. AAA98418, Apr. 1996, 1 page.*
Database UniProt [Online] Jun. 16, 2009 , SubName: Full=Protein—N(Pi)-phosphohistidine—sugar phosphotransferase; EC=<A HREF=http://srs.ebi.ac.uk/srsbin/cgi-bin/wgetz?[enzyme-ECNumber:2.7.1.69]+-e>2.7.1.69</A>; XP002545663 retrieved from EBI accession No. UNIPROT:C2H9J6 Database accession No. C2H9J6 *abstract.
Database UniProt [Online] Jun. 16, 2009 , "SubName: Full=Beta—fructofuranosidase; EC=<A HREF=http://srs.ebi.ac.uk/srsbin/cgi-bin/wgetz?[enzyme-ECNumber:3.2.1.26]+-e">3.2.1.26</A>; XP002545664 retrieved from EBI accession No. UNIPROT: C2H9J5 Database accession No. C2H9J5 *abstract.
Qin Jiayang et al: "Non-Sterilized Fermentative Production of Polymer-Grade L-Lactic Acid by a Newly Isolated Thermophilic Strain *Bacillus* sp. 2-6" PLOS One, vol. 4, No. 2, Feb. 2009.
European Search Report and the Written Opinion of the European Patent Office Patent Office in counterpart foreign application No. PCT/EP2010/060220 filed Jul. 15, 2010.
De Clerck, E., et al., Polyphasic characterization of *Bacillus coagulans* strains. Syst. Appl. Microbiol. 27:50-60, 2004.
Gasson, M.J., 1983: Plasmid complements of *Streptococcus lactis* NCDO 712 and other lactic *Streptococci* after protoplast-induced curing, J. Bacteriol. 154:1-9.
Holo, H. and I.F. Nes, High-frequency transformation, by electroporation, of *Lactococcus lactis* subsp. cremoris grown with glycine in osmotically stabilized media, Appl. Environ. Microbiol, 1989, 55:3119-3123.
Langer, S.J., A. P. Ghafoori, M. Byrd, and L. Leinwant, A genetic screen identifies novel non-compatible loxP sites, Nucleic Acids Res., 2002, 30:3067-3077.
Lambert, J.M., R.S. Bongers, and M. Kleerebezem, Cre-lox-based system for multiple gene deletions and selectable-marker removal in *Lactobacillus plantarum*, Appl. Environ. Microbiol., 2007, 73:1126-1135.
Ahschul, et al., J. Mol, Biol. 215: 403-410 (1990).
Walton et al. "Production of lactic acid from hemicellulose extracts." Society of Microbiology: May 8, 2010.
Kovacs et al. "Genetic Tool Development for a New Host for Biotechnology, the Thermotolerant Bacterium *Bacillus coagulans*." Applied and Environmental Microbiology 76.12 (2010): 4085-4088.

(Continued)

*Primary Examiner* — David J Steadman
(74) *Attorney, Agent, or Firm* — Peter J. Ims; Westman, Champlin & Koehler, P.A.

(57) ABSTRACT

A method for the construction of a moderately thermophilic *Bacillus* strain capable of utilizing sucrose as a carbon source includes the transformation of a parent moderately thermophilic *Bacillus* strain not capable of utilizing sucrose as a carbon source with a polynucleotide comprising a DNA sequence that encodes a polypeptide having sucrose-specific phosphotransferase activity and having i) an amino acid sequence of SEQ ID NO:1 or ii) an amino acid sequence with an identity of at least 70% to the sequence of SEQ ID NO:1 and/or comprising a DNA sequence that encodes a polypeptide having sucrose-6-phosphate hydrolase activity and having iii) an amino acid sequence of SEQ ID NO:2 or iv) an amino acid sequence with an identity of at least 70% to the sequence of SEQ ID NO:2.

22 Claims, 2 Drawing Sheets

(56) References Cited

OTHER PUBLICATIONS

Qin et al. "Production of l-lactic acid by a thermophilic Bacillus mutant using sodium hydroxide as neutralizing agent." Bioresource Technology 101 (2010): 7570-7576.
Su et al. "Physiological and fermentation properties of Bacillus coagulans and a mutant lacking germentative lactate dehydrogenase activity." Society of Microbiology: Jul. 31, 2010.
Bischoff et al. "Fermentation of corn fiber hydrolysate to lactic acid by the moderate thermophile Bacillus coagulans." Springer Science+Business Media B.V.: Feb. 14, 2010.
Wang et al. "Evolution of D-lactate dehydrogenase activity from glycerol dehydrogenase and its utility for D-lactate production from lignocellulose." PNAS: Nov. 22. 2011: 18920-18925.
Zhou et al. "Efficient production of L-lactic acid by newly isolated thermophilic Bacillus coagulans WCP10-4 with high glucose tolerance." Springer-Verlag Berlin Heidelberg: Jan. 25, 2013.

* cited by examiner

FERMENTATION OF MODERATELY THERMOPHILIC BACILLI ON SUCROSE

CROSS-REFERENCE TO RELATED APPLICATION

This Application is a Section 371 National Stage Application of International Application No. PCT/EP2010/060220, filed Jul. 15, 2010 and published as WO 2011/006966 A9 on Apr. 28, 2011, in English.

BACKGROUND

The discussion below is merely provided for general background information and is not intended to be used as an aid in determining the scope of the claimed subject matter.

An aspect of the present invention relates to genetic modification of moderately thermophilic *Bacillus* strains to provide the capability to utilise sucrose to *Bacillus* strains originally not possessing this capability.

Moderately thermophilic *Bacillus* species, preferably those species that are facultative anaerobic and homolactic, are ideal organisms for the industrial manufacture of lactic acid.

In an aspect of this invention, moderately thermophilic *Bacillus* species are capable of growing between 37 and 65° C. and allow industrial fermentation at temperatures above 50° C. This high fermentation temperature has several advantages when fermenting on industrial scale: less risk of infections and thus higher product purity, faster reactions etcetera. Furthermore, the nutrient requirements of these bacteria are less demanding than those of lactic acid bacteria such as *Lactobacillus* species, which also allows for relatively inexpensive industrial processes.

Moderately thermophilic *Bacillus* species include aerobic species and facultative anaerobic species. The use of facultative anaerobic species is preferred, since these species allow fermentation under anaerobic conditions, or at least under a low partial pressure of oxygen, which for industrial scale is desirable. Such conditions prevent demand for costly aeration and enable the use of low-cost media, while minimizing contamination risks or even allowing non-sterile production procedures.

It is also preferred to use moderately thermophilic *Bacillus* species that are homolactic. The homolactic nature allows the production of lactic acid from hydrocarbon sources (including hexose and pentose sugars) without the formation of more than 15 wt % side products such as formic acid and acetic acid. Genetic modification of the homolactic phenotype can be applied to convert homolactic strains into homofermentative production strains for other industrial products derivable from glycolysis, such as from phosphoenolpyruvate and/or pyruvate. Examples of these compounds are pyruvate, acetolactate, diacetyl, acetoin, 2,3-butanediol, 1,2-propanediol, acetate, formate, acetaldehyde, ethanol, L-alanine, oxaloacetate, S-malate, succinate, fumarate, 2-oxoglutarate, oxalosuccinate, isocitrate, citrate, glyoxylate.

Preferably these production strains are sporulation deficient.

Examples of moderately thermophilic and facultative anaerobic *Bacillus* species are *Bacillus coagulans*, *Bacillus smithii*, *Bacillus thermoamylovorans* and *Bacillus thermocloacae*, at least the first two species also being homolactic. A preferred species is *Bacillus coagulans*.

It is desirable in industrial fermentations to use cheap raw materials in the fermentation media. For instance, sucrose or sucrose-containing substrates are often used as low-cost carbon sources for industrial fermentations. However, it was found that not all moderately thermophilic *Bacillus* strains used for industrial fermentations possess the capability to utilise sucrose as a carbon source. This is a disadvantage, especially if such strains have undergone adaptations to improve their fermentation capability or production potential on an industrial scale. For instance, *Bacillus coagulans* strain DSM 1 appeared to be a very poor fermenter of sucrose. Only scarce growth and acid formation is observed using sucrose as sole carbon source, which is probably due to non-specific activity of systems for utilisation of other sugars.

In literature, *B. coagulans* is mentioned to be variable in sucrose utilisation capability (De Clerck, E., M. Rodriguez-Diaz, G. Forsyth, L. Lebbe, N. Logan, 2004: *Polyphasic characterization of Bacillus coagulans strains*. Syst. Appl. Microbiol. 27:50-60). However there is no information available on genes involved in sucrose catabolism and there are no genes annotated for sucrose catabolism in the *B. coagulans* 36D1 genome sequence.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present invention is to genetically modify a moderately thermophilic *Bacillus* strain originally not capable of utilising sucrose as a carbon source to provide the strain with the capacity to utilise sucrose as a carbon source. Another aspect of the invention is to avail of a method to produce a compound of interest comprising the cultivation of a moderately thermophilic *Bacillus* strain on a sucrose-containing carbon source. DETAILED DESCRIPTIONA moderately thermophilic *Bacillus* strain not capable of utilising sucrose as a carbon source may be deficient in one or more genes involved in sucrose utilisation. An aspect of the present invention now discloses genes and polypeptides involved in sucrose catabolism and obtainable from moderately thermophilic *Bacillus* species, preferably from moderately thermophilic and facultative anaerobic *Bacillus* species, most preferably from moderately thermophilic and facultative anaerobic *Bacillus* species that are homolactic.

The polypeptides surprisingly display a rather low homology to corresponding polypeptides from other *Bacillus* species, whereas a higher homology is observed with corresponding polypeptides from *Lactobacillus* species. The genes and polypeptides allow the introduction of sucrose-utilising capacity into non-sucrose-utilising moderately thermophilic *Bacillus* strains of the same (or closely related) species as the species from which the genes and polypeptides are obtainable. In particular, the genes allow the introduction of genetic material by means of self-cloning, i.e. using species-specific genetic material.

Thus, in one aspect of this invention, a method is provided for the construction of a moderately thermophilic *Bacillus* strain capable of utilising sucrose as a carbon source from a parent moderately thermophilic *Bacillus* strain not capable of utilising sucrose as a carbon source.

In particular, the moderately thermophilic *Bacillus* strain capable of utilising sucrose as a carbon source is derived from a parent moderately thermophilic *Bacillus* strain not capable of utilising sucrose as a carbon source by transformation of said parent strain with a necessary polynucleotide (gene) for achieving utilisation of sucrose. As disclosed herein, this necessary polynucleotide comprises a DNA sequence that encodes a polypeptide having sucrose-specific phosphotransferase activity and having i) an amino acid sequence of SEQ ID NO:1 or ii) an amino acid sequence with an identity of at least 70%, preferably of at least 75, 80, 85, 90, 95%, to the sequence of SEQ ID NO:1 and/or comprises a DNA sequence that encodes a polypeptide having sucrose-6-phosphate hydrolase activity and having iii) an amino acid sequence of SEQ ID NO:2 or iv) an amino acid sequence with an identity of at least 70%, preferably of at least 75, 80, 85, 90, 95%, to the sequence of SEQ ID NO:2.

Introduction of the polynucleotide for achieving utilisation of sucrose into the moderately thermophilic *Bacillus* strain of interest can be done using any suitable transformation procedure that is known to the person skilled in the art, including protoplast transformation or protoplast fusion, electroporation, biolistic transformation, conjugation, or transformation of natural competent cells. For instance, a transformation procedure as disclosed in WO 2007/085443, which is incorporated herein by reference, may be used.

The polynucleotide for achieving utilisation of sucrose may be introduced using an autonomously replicating plasmid or by chromosomal integration. The latter is preferred for industrial application, as chromosomal integration is generally regarded as more stable and will ensure a stable distribution of the polynucleotide over the progeny cells. Sucrose fermentation itself may be a selection pressure for maintenance of the polynucleotide for achieving utilisation of sucrose. Introduction of the polynucleotide into the chromosome may be done by non-homologous as well as homologous recombination.

Homologous recombination is preferred, as it opens the opportunity to introduce, to remove or to simultaneously introduce and remove a functionality into/from the bacterial chromosome. When homologous recombination is intended, the transforming polynucleotide further contains a DNA sequence that is homologous to a genomic target sequence of the specific *Bacillus* to be engineered. Any suitable genomic target sequence may be selected for this purpose. Suitable genomic target sequences are for instance located in a non-coding region of the genome. The skilled person will understand that no 100% identity is required to obtain homologous recombination. A percentage identity of about 90% will also suffice. Generally, the DNA sequence of interest to be inserted in the chromosome by homologous recombination is flanked by homologous sequences with a sufficient length to enable homologous recombination. Such a length may be at least about 100 bp, for instance between about 200 and about 1500 bp, preferably between about 200 and about 1000 bp.

To achieve expression of the polynucleotide for achieving utilisation of sucrose, the coding sequence of the polynucleotide is provided with the necessary regulatory sequences. These regulatory sequences may be the native regulatory sequences or may be heterologous to the coding sequence in question.

In a further aspect, there are provided polypeptides, i.e. a polypeptide that has sucrose-specific phosphotransferase activity and a polypeptide that has sucrose-6-phosphate hydrolase activity. The polypeptide having sucrose-specific phosphotransferase activity has i) an amino acid sequence of SEQ ID NO:1 or ii) an amino acid sequence with an identity of at least 70%, preferably at least 75%, more preferably of at least 80%, even more preferably at least 85%, even more preferably at least 90%, most preferably at least 95%, to the sequence of SEQ ID NO:1. The polypeptide having sucrose-6-phosphate hydrolase activity has i) an amino acid sequence of SEQ ID NO:2 or ii) an amino acid sequence with an identity of at least 70%, preferably at least 75%, more preferably at least 80%, even more preferably at least 85%, even more preferably at least 90%, most preferably at least 95%, to the sequence of SEQ ID NO:2.

The sucrose-specific phosphotransferase polypeptide having an amino acid sequence of SEQ ID NO:1 shares significant homology with sucrose-specific PTS system EIIBCA components from *Pediococcus pentosaceus* and *Lactobacillus plantarum* (both 62% identity at protein level) and other lactic acid bacteria. Surprisingly, homology to other *Bacillus* species is much lower, having highest identity with the *Bacillus clausii* homologue (44% identity at protein level).

The sucrose-6-phosphate hydrolase polypeptide having an amino acid sequence of SEQ ID NO:2 shares significant homology with sucrose-6-phosphate hydrolases from *Lactobacillus sakei* (50% identity at protein level) and other lactic acid bacteria. Also for this polypeptide it was surprising to see that homology to other *Bacillus* homologues was lower than that to the lactic acid bacteria. The closest *Bacillus* homologue was from *Bacillus clausii* (41% identity at protein level).

For the purpose of the present invention, the degree of identity between two amino acid sequences refers to the percentage of amino acids that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information. The BLAST algorithm parameters W, T, and X determine the sensitivity and speed of the alignment. The BLASTP program uses as defaults: Word size: 3; Expect value: 10; Hitlist size 100; Gapcosts: 11,1; Matrix: BLOSUM62.

In still a further aspect, there are provided polynucleotides encoding the polypeptides of the previous aspect, for instance a polynucleotide having a sequence according to SEQ ID NO:3 or SEQ ID NO:4.

The polypeptides and polynucleotides of the above aspects are usable to construct moderately thermophilic *Bacillus* strain capable of utilising sucrose as a carbon source, as described herein.

In still a further aspect, a method is provided for the production of a compound of interest comprising the cultivation of a moderately thermophilic *Bacillus* strain on a sucrose-containing carbon source. The method is characterized in that the moderately thermophilic *Bacillus* strain to be cultivated is derived from a parent moderately thermophilic *Bacillus* strain not capable to utilise sucrose as a carbon source by providing the parent strain with the capacity to utilise sucrose as a carbon source.

The parent moderately thermophilic *Bacillus* strain that is not capable to utilise sucrose as a carbon source is provided with the capacity to utilise sucrose as a carbon source using the method and polynucleotide(s) as described in the previous aspects. By using this methods and polynucleotide(s), the present invention advantageously allows cultivation on a sucrose-containing carbon source of moderately thermophilic *Bacillus* strains that are adapted to industrial cultivation conditions and/or selected to possess a high production potential and that originally do not possess the capability to utilize sucrose.

The carbon source that is used for cultivation of the moderately thermophilic *Bacillus* strain may contain sucrose in a level of at least 0.5% (w/w), based on the total weight of the carbon source. It is also possible to use sucrose as the sole carbon source.

The cultivation further may be performed under conventional conditions commonly known to the person skilled in the art.

After cultivation, the formed compound of interest is optionally isolated from the fermentation medium and purified when necessary. Conventional purification/isolation methods, e.g. for lactic acid, are distillation, extraction, electrodialysis, adsorption, ion-exchange, crystallization and the like, and combinations of the above-mentioned purification/isolation methods.

The compound of interest may be lactic acid. The term "lactic acid" means 2-hydroxy-propionic acid in either its free acid or salt form. Lactic acid contains a chiral carbon atom, and for that reason can exist as (R) and (S) enantiomer. The term "lactic acid" as used in this application includes the pure (R) and (S) isomers, and mixtures thereof including the racemic mixture. For the production of R-lactate, a production strain may be used that is genetically modified as described in WO 2007/085443, which is incorporated herein by reference.

The compound of interest may further be pyruvate, using a strain wherein the conversion of pyruvate to lactate is blocked. The compound of interest may further be a compound derivable from pyruvate, using a strain wherein pyruvate is redirected towards production of such a compound, including acetolactate, diacetyl, acetoin, 2,3-butanediol, 1,2-propanediol, acetate, formate, acetaldehyde, ethanol, L-alanine, oxaloacetate, S-malate, succinate, fumarate, 2-oxoglutarate, oxalosuccinate, isocitrate, citrate, glyoxylate.

EXAMPLES

Strains and Culture Conditions

B. coagulans DSM 1 was obtained from DSMZ, Braunschweig, Germany. B. coagulans was routinely grown at 50° C. under aerobic conditions (120 rpm) in BC-broth (WO 2007/085443) containing 50 g/l glucose. If appropriate, the medium was supplemented with chloramphenicol at 7 mg/l. BC plates were prepared with Gelrite as described before (WO 2007/085443). For evaluation of carbon use B. coagulans was grown on a chemically defined medium (CDM) containing per liter 2.0 g $(NH_4)_2HPO_4$, 3.5 g $(NH_4)_2SO_4$, 10 g Bis-Tris buffer (bis[2-hydroxymethyl]iminotris[hydroxymethyl]-methane), 0.5 g KCl, 0.234 g L-arginine, 0.304 g L-aspartic acid, 0.026 g L-cystine, 0.470 g glutamic acid, 0.093 g L-histidine, 0.360 g L-isoleucine, 0.581 g L-leucine, 0.111 g L-methionine, 0.197 g L-proline, 0.308 g L-serine, 0.350 g L-threonine, 0.345 g L-valine, 0.2 g $MgCl_2.6 H_2O$, 50 mg $CaCl_2.2 H_2O$, 16 mg $MnCl_2$, 7 mg $FeSO_4.7 H_2O$, 0.1 mg thiamine, 0.5 mg nicotinic acid, 0.1 mg pantothenic acid, 0.5 mg pyridoxamine, 0.5 mg pyridoxal, 0.1 mg D-biotin, 0.1 mg folic acid, 0.1 mg p-aminobenzoic acid, 0.1 mg cobalamin. If appropriate the CDM was supplemented with 5 g glucose or 5 g sucrose per liter. Lactococcus lactis MG1363 was described by Gasson (Gasson, M. J., 1983: Plasmid complements of Streptococcus lactis NCDO 712 and other lactic streptococci after protoplast-induced curing, J. Bacteriol. 154:1-9). L. lactis was routinely cultured at 30° C. in M17 broth (Difco) containing 5 g/l glucose.

Bacteria were stored in glycerolstocks, using 15% (v/v) glycerol, at −80° C.

DNA Manipulation Techniques

Standard DNA manipulation techniques were performed as described by Sambrook and Russell (J. Sambrook and D. W. Russell. 2001: Molecular Cloning, a laboratory manual. $3^{rd}$ edition. Cold Spring Harbor Laboratory Press, New York).

Large-scale plasmid DNA isolation from 100 mL culture was performed using the Jetstar 2.0 Plasmid Maxiprep Kit® (Genomed) following the instructions of the manufacturer. Small-scale plasmid DNA isolation from 1 mL culture was performed using the Nucleospin Plasmid Quick Pure® (Macherey-Nagel) kit following the instructions of the manufacturer.

Figure 2:
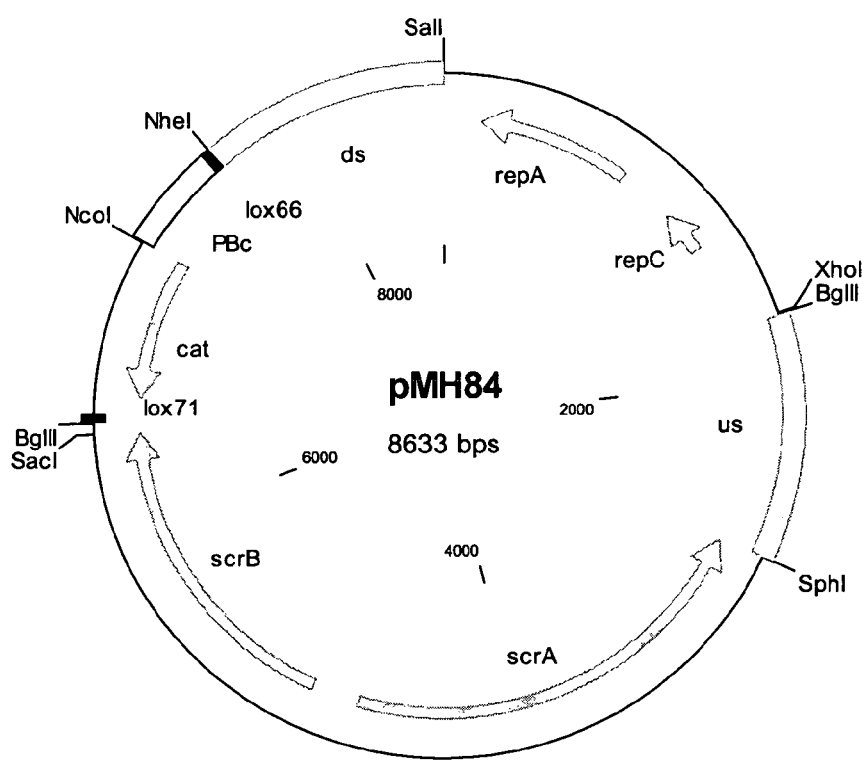
FIG. 2 shows a plasmid map of pMH84. The replication genes (repA and repB), the chloramphenicol resistance gene (cat), the sucrose PTS enzyme II gene (scrA) and the sucrose-6-phosphate hydrolase gene (scrB) are depicted by arrows. The upstream (us) and downstream (ds) regions of homology for double crossover recombination (grey), Bacillus coagulans promoter region (Bco; white), and lox sites (lox 71 and lox66; black) are boxed. For BglII and NcoI only sites relevant for the construction are included. Aspects of the present invention are elucidated by the following Examples, without being limited thereto or thereby.

L. lactis served as intermediate host during construction of the integration plasmid pMH84 (FIG. 2). Preparation of L. lactis competent cells and electroporation were performed as described by Holo and Nes (Holo, H. and I. F. Nes, 1989: High-frequency transformation, by electroporation, of Lactococcus lactis subsp. cremoris grown with glycine in osmotically stabilized media, Appl. Environ. Microbiol. 55:3119-3123).

B. coagulans was transformed by electroporation as described in WO 2007/085443.

PCR reactions for cloning purposes were performed with the high-fidelity Pwo polymerase (Roche) following the instructions of the manufacturer.

Colony-PCR analysis was used to demonstrate the presence of pNW33N in the chloramphenicol resistant colonies as described in WO 2007/085443.

Fermentations

B. coagulans batch fermentations were performed in screw-cap tubes (13 mL) with 10 ml of BC broth or CDM at 50° C.

Samples were withdrawn at the end of fermentation for measurement of turbidity at 600 nm, pH, and organic acid content in the fermentation broth. For the latter, samples were centrifuged and remaining debris in the supernatant was removed by filtration using a Millex GP 0.22 μm filter® (Millipore). Filtrate was frozen until further analysis.

Organic acids (formic acid, acetic acid, propionic acid, ethanol, butyric acid, pyruvic acid, lactic acid, 2-hydroxy butyric acid, glycolic acid, oxalic acid, sorbic acid, fumaric acid, succinic acid, benzoic acid, maleic acid, malic acid, citric acid) were measured using a derivatisation and GLC. R- and S-lactates were methylated to methyl-lactate and measured by headspace analysis on a chiral column.

Example 1

Construction of a B. coagulans Sucrose Utilization Integration Plasmid

Figure 1:
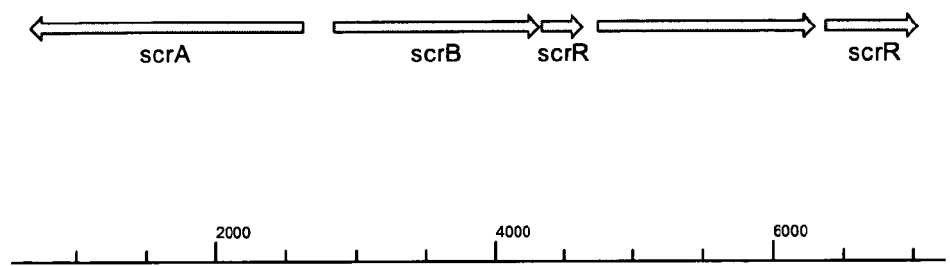
FIG. 1 shows the genomic map of the sucrose operon from Bacillus coagulans, depicting the sucrose PTS enzyme II gene (scrA) and the sucrose-6-phosphate hydrolase gene (scrB).

Random sequence analysis of a selected sucrose fermenting B. coagulans strain revealed a region of two genes with sequence homology to sucrose PTS enzyme II and sucrose-6-phosphate hydrolase genes (scrA and scrB respectively). A genetic map of the region is shown in FIG. 1. A DNA fragment containing scrAB gene cluster and their promoters (depicted in SEQ ID NO:5) was generated with high fidelity PCR using the primers 5'-AGTACT GCATGCTTAAAGAGTAGCTTTCGGTGTTAAAGTG-3' (introducing an SphI site, SEQ ID NO:6) and 5'-AGTACT GAGCTCCTATTTATTAATAGAATGAAGACTCCAGTAG TTCCC-3' (introducing a SacI site, SEQ ID NO:7) in combination with genomic DNA from a sucrose-fermenting B. coagulans strain as template DNA. Alternatively the scrAB gene cluster can be generated as synthetic DNA having the sequence depicted in SEQ ID NO:5. A B. coagulans integration plasmid was modified to allow integration of the scrAB gene cluster in the B. coagulans DSM 1 chromosome. Fragments of 1.0 kb upstream and downstream of the chromosomal integration site were used for recombination. The integration vector, pMH84 (FIG. 2), is based on the lactococcal cloning vector pMH3 (WO 2007/085443) and has a thermosensitive replicon in *B. coagulans*. First the cat promoter was replaced by a *B. coagulans* promoter. To this end the pMH3 BglII-SalI fragment containing the cat gene was replaced by a fusion PCR product of a constitutive *B. coagulans* promoter translationally fused to the cat gene simultaneously introducing an NcoI site overlapping the cat start codon (SEQ ID NO:18). The promoter part was generated using primer combination (forward) 5'-CGC GTCGACTGTGGATAAGACAACAGGATTCGTATG-3' (introducing a SalI site, SEQ ID NO:8) and (reverse) 5'-CTAAATCAATTTTATTAAAGT CCATGGGTCCACCCCGTTCTTTTCTTTTTGTG-3' (introducing an NcoI site, SEQ ID NO:9) with genomic DNA from a sucrose-fermenting *B. coagulans* strain as template DNA. The cat gene was generated using primer combination (forward) 5'-CACAAAAAGAAAAGAACGGGGTGGAC CCATGGACTTTAATAAAATTGATTTAG-3' (introducing an NcoI site, SEQ ID NO:10) and (reverse) 5'-CGC AGATCTCCTTCTTCAACTAACGGG-3' (introducing a BglII site, SEQ ID NO:11) using pMH3 as a template. Both products were used as template in a new PCR reaction using the promoter forward and cat reverse primers. This fragment can also be generated as synthetic DNA having the sequence depicted in SEQ ID NO:18. The resulting plasmid was designated pMH71. To enable multiple use of the Cre-lox system, lox66 and lox71 sites (Langer, S. J., A. P. Ghafoori, M. Byrd, and L. Leinwand, 2002: *A genetic screen identifies novel non-compatible loxP sites*, Nucleic Acids Res. 30:3067-3077, Lambert, J. M., R. S. Bongers, and M. Kleerebezem, 2007: *Cre-lox-based system for multiple gene deletions and selectable-marker removal in Lactobacillus plantarum*, Appl. Environ. Microbiol. 73:1126-1135.) flanking the promoter-cat region were introduced by PCR using primers 5'-CCC GTCGACGCTAGCTACCGT TCGTATAATGTATGCTATA CGAAGTTATGTGGATAAGACAACAGGA TTCG-3' (introducing the lox66, SalI and NheI sites, SEQ ID NO:12) and 5'-CGC AGATCTACCGTTCGTATAGCATACATTATACGAAGT TATCCTTCTTCAACTAACGGGGCAGGT TAG-3' (introducing the lox71 and BglII sites, SEQ ID NO:13) and pMH71 as template. The resulting PCR product was digested with BglII-SalI and used to exchange with the BglII-SalI promoter-cat region of pMH71, resulting in plasmid pMH77. The upstream fragment of the integration site was generated by PCR using primers 5'-CGC CTCGAGAGATCTGGCCGGGCTTTATGGGAGG-3' (introducing XhoI and BglII sites, SEQ ID NO:14) and 5'-GCC GAGCTCGCATGCCCCTGATCAACCGGGTCAGTGC (introducing SacI and SphI sites, SEQ ID NO:15) and *B. coagulans* DSM 1 chromosomal DNA as template. The PCR product was cloned in pMH77 using SacI and XhoI. This resulted in pMH82. The downstream fragment of the integration site was generated by PCR using primers 5'-CCC GCTAGCCGTTTCAATCACATAGTCGTATTG (introducing an NheI site, SEQ ID NO:16) and 5'-CCG GTCGACGGCCTTCATGTGCTTTTGCCGCAAATTC (introducing a SalI site, SEQ ID NO:17) and *B. coagulans* DSM 1 chromosomal DNA as template. The PCR product was cloned in pMH82 as SalI-NheI fragment, resulting in pMH83. The DNA fragment containing the scrAB genes was cloned as SphI and SacI fragment in pMH83 digested with the same enzymes, which resulted in integration vector pMH84 (FIG. 2). Plasmid pMH84 was isolated and the integrity of the scrAB gene cluster, the upstream and downstream regions, and the lox sites was confirmed by DNA sequence analysis.

Example 2

Genomic Integration of scrAB in *B. coagulans* DSM 1

For genomic integration of the scrAB genes into *B. coagulans* DSM 1, plasmid pMH84 was transformed to this strain by electroporation and plated on BC plates supplemented with chloramphenicol. Transformants were screened for the presence of the plasmid by colony PCR. Positive colonies were cultured for plasmid isolation and the integrity of the plasmid was confirmed by restriction analysis. One transformant was selected for further experiments. Integration of the sucrose genes by double crossover exchange was established after cultivation at 60° C. and selection for chloramphenicol resistant colonies. One integrant was selected for further studies and stored as glycerolstock. The correct integration was confirmed by PCR analysis and sequence analysis of the fusion sites. This strain was designated *B. coagulans* DSM 1::scrAB.

Example 3

Sucrose Fermentation with *B. coagulans*

In this experiment the inventors demonstrate how *B. coagulans* strains that are not capable of efficient sucrose fermentation can be modified to become sucrose-fermenting. *B. coagulans* strains DSM 1 and DSM 1::scrAB were inoculated from glycerolstock in 10 ml BC broth without sugar and incubated at 50° C. at 120 rpm. Overnight cultures were transferred (2% v/v) to 10 ml CDM supplemented with glucose. After overnight incubation the cultures were pelleted and the pellets were resuspended in 10 ml CDM without sugar. For each strain three triplicate portions of 10 ml CDM supplemented with either 5 g glucose per liter, 5 g sucrose per liter, or no sugar were inoculated (2% v/v) from the resuspended cultures. After 50 h static incubation in screw cap tubes the turbidity at 600 nm, the pH, and the organic acid content of the broth supernatant were determined (Table 1). The results demonstrate that sugar is required for proper anaerobic growth and that *B. coagulans* DSM 1::scrAB is able to ferment sucrose to lactic acid, while *B. coagulans* DSM 1 is not. Absence of sugar resulted in no growth and no acidification for both *B. coagulans* strains. In the presence of sucrose DSM 1 showed no growth and no acidification, while *B. coagulans* DSM 1::scrAB had good growth and acidification. Lactic acid was the only organic acid that was detected in the culture supernatants. This demonstrates that introducing the *B. coagulans* scrAB gene cassette is sufficient for efficient sucrose fermentation with *B. coagulans*.

TABLE 1

Fermentation characteristics after 50 h incubation[a]

| | Strain | | | | | |
|---|---|---|---|---|---|---|
| | *B. coagulans* DSM 1::scrAB | | | *B. coagulans* DSM 1 | | |
| Carbon added | Glucose | Sucrose | None | Glucose | Sucrose | None |
| Turbidity at 600 nm | 0.6 | 0.8 | 0.0 | 0.7 | 0.1 | 0.0 |
| pH | 4.4 | 4.5 | 6.5 | 4.4 | 6.5 | 6.5 |
| Lactic acid | 0.41 | 0.36 | N.D. | 0.40 | N.D. | N.D. |

[a]Data are mean from 3 fermentations. Organic acid concentrations are given in % (w/w). N.D., not determined. Formic acid (<0.02%), acetic acid (<0.02%), propionic acid (<0.02%), butyric acid (<0.01%), pyruvic acid (<0.02%), 2-hydroxybutyric acid (<0.01%), glycolic acid (<0.20%), oxalic acid (<0.02%), sorbic acid (<0.01%), fumaric acid (<0.02%), succinic acid (<0.02%), benzoic acid (<0.03%), and maleic acid (<0.02%) were below detection limits.

The invention claimed is:

1. A method for the production of lactic acid, the method comprising the cultivation of a moderately thermophilic *Bacillus* strain on a sucrose carbon source, wherein the moderately thermophilic *Bacillus* strain is capable of producing lactic acid and growing between 37° C. and 65° C., wherein the moderately thermophilic *Bacillus* strain is derived from a parent moderately thermophilic *Bacillus* strain that is not capable of utilising sucrose as a carbon source by transformation of said parent strain with a polynucleotide comprising a DNA sequence that encodes a polypeptide having sucrose-specific phosphotransferase activity and comprising an amino acid sequence with an amino acid sequence identity of at least 85% to the amino acid sequence of SEQ ID NO:1 and comprising a DNA sequence that encodes a polypeptide having sucrose-6-phosphate hydrolase activity and comprising an amino acid sequence with an amino acid sequence identity of at least 85% to the amino acid sequence of SEQ ID NO:2.

2. The method according to claim 1, wherein the moderately thermophilic *Bacillus* strain is facultative anaerobic.

3. The method according to claim 1, wherein the moderately thermophilic *Bacillus* strain is homolactic.

4. The method according to claim 1, wherein the moderately thermophilic *Bacillus* strain is *Bacillus coagulans*.

5. The method according to claim 1, wherein the polypeptide having sucrose-specific phosphotransferase activity comprises the amino acid sequence of SEQ ID NO:1.

6. The method according to claim 1, wherein the polypeptide having sucrose-specific phosphotransferase activity comprises an amino acid sequence with an amino acid sequence identity of at least 90% to the amino acid sequence of SEQ ID NO: 1.

7. The method according to claim 1, wherein the polypeptide having sucrose-6-phosphate hydrolase activity comprises the amino acid sequence of SEQ ID NO:2.

8. The method according to claim 1, wherein the polypeptide having sucrose-6-phosphate hydrolase activity comprises an amino acid sequence with an amino acid sequence identity of at least 90% to the amino acid sequence of SEQ ID NO:2.

9. A method for the production of pyruvate, the method comprising the cultivation of a moderately thermophilic *Bacillus* strain on a sucrose carbon source, wherein the moderately thermophilic *Bacillus* strain is capable of producing pyruvate and growing between 37° C. and 65° C., wherein the moderately thermophilic *Bacillus* strain is derived from a parent moderately thermophilic *Bacillus* strain that is not capable of utilising sucrose as a carbon source by transformation of said parent strain with a polynucleotide comprising a DNA sequence that encodes a polypeptide having sucrose-specific phosphotransferase activity and comprising an amino acid sequence with an amino acid sequence identity of at least 85% to the amino acid sequence of SEQ ID NO:1 and comprising a DNA sequence that encodes a polypeptide having sucrose-6-phosphate hydrolase activity and comprising an amino acid sequence with an amino acid sequence identity of at least 85% to the amino acid sequence of SEQ ID NO:2.

10. The method according to claim 9, wherein the moderately thermophilic *Bacillus* strain is facultative anaerobic.

11. The method according to claim 9, wherein the moderately thermophilic *Bacillus* strain is *Bacillus coagulans*.

12. The method according to claim 9, wherein the polypeptide having sucrose-specific phosphotransferase activity comprises the amino acid sequence of SEQ ID NO:1.

13. The method according to claim 9, wherein the polypeptide having sucrose-specific phosphotransferase activity comprises an amino acid sequence with an amino acid sequence identity of at least 90% to the amino acid sequence of SEQ ID NO: 1.

14. The method according to claim 9, wherein the polypeptide having sucrose-6-phosphate hydrolase activity comprises the amino acid sequence of SEQ ID NO:2.

15. The method according to claim 9, wherein the polypeptide having sucrose-6-phosphate hydrolase activity comprises an amino acid sequence with an amino acid sequence identity of at least 90% to the amino acid sequence of SEQ ID NO:2.

16. A method for the production of a compound of interest selected from the group consisting of succinate, formate, acetate, ethanol, acetoin, and 2,3-butanediol, the method comprising the cultivation of a moderately thermophilic *Bacillus* strain on a sucrose carbon source, wherein the moderately thermophilic *Bacillus* strain is capable of producing succinate, formate, acetate, ethanol, acetoin, and 2,3-butanediol and growing between 37° C. and 65° C., wherein the moderately thermophilic *Bacillus* strain is derived from a parent moderately thermophilic *Bacillus* strain that is not capable of utilising sucrose as a carbon source by transformation of said parent strain with a polynucleotide comprising a DNA sequence that encodes a polypeptide having sucrose-specific phosphotransferase activity and comprising an amino acid sequence with an amino acid sequence identity of at least 85% to the amino acid sequence of SEQ ID NO:1 and comprising a DNA sequence that encodes a polypeptide having sucrose-6-phosphate hydrolase activity and comprising an amino acid sequence with an amino acid sequence identity of at least 85% to the amino acid sequence of SEQ ID NO:2.

17. The method according to claim 16, wherein the moderately thermophilic *Bacillus* strain is facultative anaerobic.

18. The method according to claim 16, wherein the moderately thermophilic *Bacillus* strain is *Bacillus coagulans*.

19. The method according to claim 16, wherein the polypeptide having sucrose-specific phosphotransferase activity comprises the amino acid sequence of SEQ ID NO:1.

20. The method according to claim 16, wherein the polypeptide having sucrose-specific phosphotransferase activity comprises an amino acid sequence with an amino acid sequence identity of at least 90% to the amino acid sequence of SEQ ID NO: 1.

21. The method according to claim 16, wherein the polypeptide having sucrose-6-phosphate hydrolase activity comprises the amino acid sequence of SEQ ID NO:2.

22. The method according to claim 16, wherein the polypeptide having sucrose-6-phosphate hydrolase activity comprises an amino acid sequence with an amino acid sequence identity of at least 90% to the amino acid sequence of SEQ ID NO:2.

* * * * *

SEQUENCE LISTING

<160> NUMBER OF SEQ ID NOS: 18

<210> SEQ ID NO 1
<211> LENGTH: 656
<212> TYPE: PRT
<213> ORGANISM: Bacillus coagulans

<400> SEQUENCE: 1

```
Met Asn His Ala Lys Val Ala Lys Asp Val Leu Asn Ala Leu Asn Gly
  1               5                  10                  15

Lys Asp Asn Ile Lys Ala Ala His Cys Ala Thr Arg Leu Arg Leu
                 20                  25                  30

Val Ile Asn Asp Glu Ser Lys Ile Asp Gln Lys Ala Leu Asp Ala His
                 35                  40                  45

Pro Asp Val Lys Gly Thr Phe Lys Thr Asn Gly Gln Tyr Gln Ile Ile
 50                  55                  60

Ile Gly Pro Gly Asp Val Asp Lys Val Tyr Ala Glu Leu Ile Lys Leu
 65                  70                  75                  80

Thr Gly Leu Pro Asp Met Thr Thr Glu Asp Val Lys Lys Thr Ser Asn
                 85                  90                  95

Glu Lys Gln Gly Asn Val Leu Leu Arg Leu Ile Lys Val Leu Ser Asp
                100                 105                 110

Ile Phe Val Pro Ile Ile Pro Ala Leu Val Ala Gly Gly Leu Leu Met
                115                 120                 125

Ala Leu Asn Asn Val Leu Thr Ala Glu His Leu Phe Thr Lys Lys Ala
                130                 135                 140

Ile Val Glu Leu Tyr Pro Gly Leu Lys Asp Ile Ala Ser Phe Ile Asn
145                 150                 155                 160

Thr Met Ser Ala Ala Pro Phe Thr Phe Leu Pro Val Leu Ile Gly Tyr
                165                 170                 175

Ser Ala Thr Lys Arg Phe Gly Gly Asn Pro Tyr Leu Gly Ala Ala Met
                180                 185                 190

Gly Met Ile Met Val Ser Pro Ala Leu Thr Ser Gly Tyr Asp Val Val
                195                 200                 205

Ser Ala Lys Ala Ser Gly Glu Leu Ala Tyr Trp His Ile Phe Gly Leu
                210                 215                 220

Lys Val Ala Gln Ala Gly Tyr Gln Gly Ser Val Leu Pro Val Leu Val
225                 230                 235                 240

Val Ser Trp Ile Leu Ala Lys Leu Glu Lys Phe Phe His Lys Tyr Ile
                245                 250                 255

Ser Asn Ala Phe Asp Phe Thr Phe Thr Pro Met Leu Ala Ile Ile Ile
                260                 265                 270

Thr Gly Phe Leu Thr Phe Thr Phe Val Gly Pro Val Met Arg Asp Val
                275                 280                 285

Ser Asp Gly Leu Thr Asn Gly Ile Met Trp Leu Tyr Asn Ala Thr Gly
                290                 295                 300

Ala Val Gly Thr Ala Ile Phe Gly Leu Phe Tyr Ser Pro Ile Val Ile
305                 310                 315                 320

Thr Gly Leu His Gln Ser Phe Pro Ala Ile Glu Thr Thr Leu Leu Ala
                325                 330                 335

Asp Ile Ala Lys Thr Gly Gly Ser Phe Val Leu Pro Ile Ala Ser Met
                340                 345                 350

Ala Asn Ile Ala Gln Gly Ala Ala Cys Leu Ala Val Phe Phe Ile Thr
                355                 360                 365
```

```
Lys Ser Lys Lys Gln Lys Ser Leu Ser Ser Ala Ser Ile Ser Ala
    370                 375                 380

Leu Leu Gly Ile Thr Glu Pro Ala Ile Phe Gly Ile Asn Leu Lys Leu
385                 390                 395                 400

Arg Tyr Pro Phe Phe Cys Ala Met Val Ala Ser Gly Ile Ala Ser Ile
                405                 410                 415

Phe Ile Gly Met Phe His Val Leu Ser Val Ser Met Gly Pro Ala Ser
            420                 425                 430

Val Ile Gly Phe Ile Cys Ile Arg Ser Gln Ser Ile Leu Pro Phe Val
            435                 440                 445

Met Ser Gly Ala Ile Ser Phe Val Ile Ala Phe Thr Thr Thr Tyr Ile
    450                 455                 460

Tyr Gly Arg Arg Ala Ala Ala Lys Glu Gln Asn Thr Ile Thr Asn Glu
465                 470                 475                 480

Arg Val Ser Gly Lys Glu Gln Ile Gly Glu Thr Ala Ala Ser Ala Thr
                485                 490                 495

Ala Pro Ala Gly Asn Ile Ile Ile Phe Ala Pro Val Glu Gly Glu Thr
            500                 505                 510

Met Ser Leu Lys Asn Val Lys Asp Lys Leu Phe Ser Ser Glu Leu Met
    515                 520                 525

Gly Lys Gly Ala Ala Ile Met Pro Lys Asn Gly Asp Val Tyr Ala Pro
530                 535                 540

Cys Asp Gly Ile Leu Thr Thr Val Phe Asp Thr His His Ala Tyr Gly
545                 550                 555                 560

Ile Lys Thr Glu Asp Gly Ala Glu Ile Leu Ile His Ile Gly Ile Asp
                565                 570                 575

Thr Val Asn Leu Lys Gly Glu Tyr Phe Thr Ser Tyr Val Glu Lys Gly
            580                 585                 590

Gln Thr Val Asn Gln Gly Asp Lys Leu Cys Ser Phe Asp Leu Glu Lys
            595                 600                 605

Ile Lys Glu Leu Gly Tyr Asp Pro Thr Val Ile Thr Val Val Thr Asn
    610                 615                 620

Thr Ala Asp Tyr Ala Ala Val Glu Gly Phe Asn His Asp His Asp Lys
625                 630                 635                 640

Val Lys Gln Gly Ser Gln Phe Ile Thr Leu Thr Pro Lys Ala Thr Leu
                645                 650                 655

<210> SEQ ID NO 2
<211> LENGTH: 493
<212> TYPE: PRT
<213> ORGANISM: Bacillus coagulans

<400> SEQUENCE: 2

Met Glu Trp Asn Arg Ala Leu Arg Tyr Lys Asn Leu Asn Glu Trp Ser
1               5                   10                  15

Glu Glu Glu Lys Lys His Leu Leu Leu Gln Ile Glu Asn Ser Pro Trp
            20                  25                  30

Arg Leu His Tyr His Ile Gln Pro Glu Ser Gly Leu Leu Asn Asp Pro
        35                  40                  45

Asn Gly Phe Ser Phe Phe Asn Asp Glu Trp His Leu Phe Tyr Gln Asn
    50                  55                  60

Tyr Pro Met Gly Pro Val His Gly Leu Lys Cys Trp Tyr His Leu Ser
65                  70                  75                  80

Ser Lys Asp Leu Ile His Trp Lys Gly Lys Gly Leu Ala Ile Leu Pro
                85                  90                  95
```

Asp Thr Glu Tyr Asp Ser His Gly Cys Tyr Ser Gly Ser Ala Ile Pro
            100                 105                 110

Val Glu Asp Arg Leu Phe Ile Met Tyr Thr Gly Asn Val Arg Asp Lys
        115                 120                 125

Asn Trp Asn Arg Phe Ser Tyr Gln Leu Gly Ala Trp Met Asp Lys Lys
130                 135                 140

Gly Arg Ile Ser Lys Leu Lys Thr Pro Leu Ile Ala Lys Gln Pro Glu
145                 150                 155                 160

Asn Tyr Thr Asp His Phe Arg Asp Pro Gln Ile Ile Arg Tyr His Asn
                165                 170                 175

Ser Tyr Tyr Ala Leu Ile Gly Ala Gln Thr Lys Gln Lys Glu Gly Asn
            180                 185                 190

Ile Leu Val Tyr Gln Ser Lys Asp Leu Lys Asn Trp Glu Phe Asn Gly
        195                 200                 205

Pro Leu Glu Leu Pro Leu Lys Asn Leu Gly Tyr Met Ile Glu Cys Pro
210                 215                 220

Asn Ile Val Trp Val Asp Gln Lys Pro Val Leu Ile Phe Cys Pro Gln
225                 230                 235                 240

Gly Leu Asp Gln Asn Ile Leu His Tyr Gln Asn Ile Tyr Pro Asn Thr
                245                 250                 255

Tyr Leu Ile Gly Asp Thr Phe Asp Pro Glu Lys Asn Arg Phe Glu Ser
            260                 265                 270

Lys Tyr Leu Leu His Asn Leu Asp Glu Gly Phe Asp Ile Tyr Ala Thr
        275                 280                 285

Gln Ala Phe Asn Ala Pro Asp Gly Arg Thr Leu Ala Val Ser Trp Ile
290                 295                 300

Gly Leu Pro Glu Ile Asp Tyr Pro Thr Asp Gln Tyr Gly Trp Ala His
305                 310                 315                 320

Cys Leu Ser Leu Ile Lys Glu Leu Lys Ile Gln Asp Gly His Leu Tyr
                325                 330                 335

Gln Phe Pro Val Lys Glu Thr Glu Ser Leu Arg Gly Arg Lys Ile Glu
            340                 345                 350

Leu Asp Gly Val Leu Thr Glu Gln Thr Gln Leu Ile Leu Asn Gln Asn
        355                 360                 365

Glu Thr Ala Tyr Glu Leu Glu Ile Ile Leu Lys Gly Asn Gly Glu Gly
370                 375                 380

Lys Leu Gln Leu Ala Ser Asp Gly His Gln Ala Leu Asn Leu Ile Phe
385                 390                 395                 400

Asn Phe Ala Asp Gly Thr Leu Val Leu Asp Arg Ser His Ala Gly Ile
                405                 410                 415

Pro Phe Ala Gln Gln Tyr Gly Thr Ser Arg Thr Val Gln Ile Pro Lys
            420                 425                 430

Asn Thr Pro Leu Asn Leu His Ile Phe Met Asp Ala Ser Val Val Glu
        435                 440                 445

Ile Phe Leu Asn His Gly His Asp Val Leu Thr Ser Arg Leu Phe Pro
450                 455                 460

Ser Lys Lys Gln Thr Lys Ile Phe Leu Glu Thr Asn His His Leu Ala
465                 470                 475                 480

Tyr Asn Gly Asn Tyr Trp Ser Leu His Ser Ile Asn Lys
                485                 490

<210> SEQ ID NO 3
<211> LENGTH: 1971
<212> TYPE: DNA

<213> ORGANISM: Bacillus coagulans

<400> SEQUENCE: 3

```
atgaaccatg caaaggttgc aaaagacgtg ttaaacgctt taaatggcaa agataatata      60
aaagctgcag cccactgcgc gacaaggctg cgcttagtta tcaatgatga atcaaaaata     120
gaccaaaaag cattggatgc gcatccggat gtaaaggta catttaaaac aaacggccag      180
taccaaatta ttataggacc gggggatgtc gataaagttt atgctgaatt gatcaaatta     240
accggccttc cggatatgac aacggaggat gtgaaaaaaa cttcgaatga aaagcaggga     300
aatgtattat taagattaat caaggtatta tctgatattt ttgttccaat tattcctgca     360
cttgttgccg gcggtttgct gatggcttta aacaatgtat tgacagcgga acacctattc     420
acaaagaagg caatagtgga attgtacccg ggactgaaag atatagcgtc atttatcaat     480
accatgtcgg ctgccccatt tactttcttg ccggttttaa tcggatattc cgcaaccaaa     540
cggtttggtg ggaatccgta tttaggagct gctatgggga tgatcatggt atctcctgca     600
ttgacaagcg ggtatgatgt tgttagcgca aaagcatcag gggagttggc ttattggcat     660
atttttggat taaagtcgc gcaggccggt taccaaggct ctgtcttgcc ggtattggta      720
gtttcatgga ttttagctaa attagagaaa tttttccata aatatatttc aaatgcattt     780
gattttacgt tcacaccgat gcttgccatt atcattacag gatttctaac gtttacattt     840
gttgggcctg ttatgcgtga tgtgagtgat gggttaacca atggaattat gtggttatat     900
aatgcaacag gcgcggttgg aactgcaatc tttggactgt tttattcacc gattgtcatt     960
accggtctgc atcaaagttt tcctgcaatt gaaaccacac ttttggctga tattgcaaaa    1020
accggcggat cgtttgtatt accaatcgcc tctatggcta atattgcgca aggtgctgct    1080
tgtcttgccg tattctttat tacaaaaagt aaaaaacaaa aaagcttatc ttcttcagca    1140
agtatttcag ctcttttggg gattacagaa ccggctattt tcggattaa cttgaaatta     1200
aggtatccgt tcttttgtgc aatggttgct tccggtattg cttctatatt tattggcatg    1260
ttccatgtgt tatcagtttc aatgggacct gcaagtgtaa ttggttttat ttgcattcgc    1320
tcacaatcta tcttgccttt tgtcatgagt ggcgcaataa gttttgttat cgccttcaca    1380
acaacgtata tatatggaag acgggcggcg gcaaaggaac aaaatacgat tacgaatgaa    1440
cgggtatctg gaaaagaaca aataggagaa acggctgctt cggctacggc ccctgctggt    1500
aatatcatca ttttttgcccc ggttgaaggt gaaacaatga gcttaaaaaa tgtgaaggat    1560
aaattatttt catctgaatt aatgggtaaa ggggcagcca tcatgccgaa aaacggcgat    1620
gtctatgctc cttgtgacgg aatttttgacc acggtatttg atacacatca tgcatacggc    1680
attaaaacgg aagatggagc agaaatttta attcacattg gtattgacac ggttaatctg    1740
aaaggcgaat attttacaag ttacgtagaa aaaggtcaga cggtaaacca aggcgacaaa    1800
ctatgcagtt tgatctgga gaaaattaaa gaacttggtt atgatccaac cgtgatcacc    1860
gtcgtgacca acacagcaga ttatgcggct gttgaaggat ttaatcatga tcatgataag    1920
gtaaaacagg ggagccagtt catcactta acaccgaaag ctactcttta a              1971
```

<210> SEQ ID NO 4
<211> LENGTH: 1482
<212> TYPE: DNA
<213> ORGANISM: Bacillus coagulans

<400> SEQUENCE: 4

```
atggaatgga atcgagcatt acgttataaa aatctaaatg agtggtctga ggaagaaaaa       60
```

```
aagcatttac ttcttcaaat agaaaattct ccgtggcggc tgcattacca tattcaacct      120
gaaagcggat tgttgaatga tccaaacgga ttttcttttt ttaatgatga atggcatcta      180
ttttatcaaa attatccgat ggggcctgtc catggtttaa aatgctggta tcatcttagt      240
tcaaaagatc ttatccattg gaaagggaag gggctggcca tattgccgga tacagagtat      300
gacagtcacg gctgctactc cggatctgca atcccggttg aagaccgttt atttatcatg      360
tatacaggaa acgtccgaga taaaaactgg aacagattct cttaccagct tggagcgtgg      420
atggataaaa aaggtcggat tccaaatta aaaactccat taattgcaaa acagccagaa       480
aattacacgg accatttcag ggatccgcaa attatccgtt atcataattc ttactatgct      540
ttgatcggtg cccagacgaa acaaaaagag gggaatatct tggtttacca atccaaagac      600
ctgaaaaact gggaattcaa cggaccgctt gaattaccgt taagaatttt gggatatatg      660
attgaatgcc cgaatatcgt atgggtggat caaaagccgg tccttatatt ctgcccgcaa      720
ggcctcgacc aaaatatttt acactatcaa aatatttatc ccaacactta cttaattggg      780
gatacgttcg accctgagaa aaaccgtttt gaatctaaat atctcctgca taatttggat      840
gaaggattcg atatttacgc tacgcaggcc tttaacgcac cggacgggcg cacacttgca      900
gtcagctgga tcggccttcc tgaaatcgat tatccgacag atcagtacgg ttgggcgcat      960
tgcttgagtt taatcaaaga attgaaaata caggacggcc atctttatca atttcctgta     1020
aaagaaacag agagccttcg cggaaggaaa attgaattgg acggggtctt aacagaacag     1080
acccagctga tattgaatca aaatgagaca gcttatgaat tggaaatcat tctgaaaggg     1140
aacggggaag gtaaattaca attggcttcg gacgggcatc aagcgttaaa tcttatttcc     1200
aactttgctg atggaacatt ggtcctggac cgcagccatg cgggtatccc ttttgcacag     1260
caatacggaa cttccagaac cgtccaaatt ccaaaaaata ccccgctgaa cctgcatatt     1320
tttatggatg cttctgtcgt tgaattttt ttaaaccatg gacacgatgt gttaacatct     1380
cgtctctttc caagcaaaaa acaaacaaag atcttcttgg aaacaaacca tcatttagct     1440
tataatggga actactggag tcttcattct attaataaat ag                       1482
```

<210> SEQ ID NO 5
<211> LENGTH: 3678
<212> TYPE: DNA
<213> ORGANISM: Bacillus coagulans

<400> SEQUENCE: 5

```
gagctcctat ttattaatag aatgaagact ccagtagttc ccattataag ctaaatgatg       60
gtttgtttcc aagaagatct ttgtttgttt tttgcttgga agagacgag atgttaacac       120 atcgtgtcca tggtttaaaa aaatttcaac gacagaagca tccataaaaa tatgcaggtt      180
cagcggggta tttttggaa tttggacggt tctggaagtt ccgtattgct gtgcaaaagg       240
gatacccgca tggctgcggt ccaggaccaa tgttccatca gcaaagttga aaataagatt      300
taacgcttga tgcccgtccg aagccaattg taatttacct tccccgttcc ctttcagaat      360
gatttccaat tcataagctg tctcattttg attcaatatc agctgggtct gttctgttaa      420
gaccccgtcc aattcaattt tccttccgcg aaggctctct gtttctttta caggaaattg      480
ataaagatgg ccgtcctgta ttttcaattc tttgattaaa ctcaagcaat gcgcccaacc      540
gtactgatct gtcggataat cgatttcagg aaggccgatc cagctgactg caagtgtgcg      600
cccgtccggt gcgttaaagg cctgcgtagc gtaaatatcg aatccttcat ccaaattatg      660
caggagatat ttagattcaa aacggttttt ctcagggtcg aacgtatccc caattaagta      720
```

```
agtgttggga taaatatttt gatagtgtaa aatattttgg tcgaggcctt gcgggcagaa    780
tataaggacc ggcttttgat ccacccatac gatattcggg cattcaatca tatatcccaa    840
attctttaac ggtaattcaa gcggtccgtt gaattcccag ttttcaggt ctttggattg     900 gtaaaccaag atattcccct cttttgttt cgtctgggca ccgatcaaag catagtaaga    960
attatgataa cggataattt gcggatccct gaaatggtcc gtgtaatttt ctggctgttt   1020
tgcaattaat ggagttttta atttggaaat ccgaccttt ttatccatcc acgctccaag   1080
ctggtaagag aatctgttcc agttttatc tcggacgttt cctgtataca tgataaataa    1140
acggtcttca accgggattg cagatccgga gtagcagccg tgactgtcat actctgtatc   1200
cggcaatatg ccagcccct tcccttcca atggataaga tcttttgaac taagatgata    1260
ccagcatttt aaaccatgga caggccccat cggataattt tgataaaata gatgccattc   1320
atcattaaaa aaagaaaatc cgtttggatc attcaacaat ccgctttcag gttgaatatg   1380
gtaatgcagc cgccacggag aattttctat ttgaagaagt aaatgctttt ttcttcctc    1440 agaccactca tttagatttt tataacgtaa tgctcgattc cattccatat atataaaacc   1500
tccccaaatt caaggaaagc gttctcctgg atttaatgta ctgtaaacaa agtgatatgt   1560
caaccgtata acatacaaaa tatcttaaat gatggtaaaa cataaaaaaa taataaaaaa   1620
tatgataaac gcttgacata taataaaaag atagtatatt agtatgtgaa acgattacaa   1680
aaatatgaaa gggtgtacac gatgaaccat gcaaaggttg caaaagacgt gttaaacgct   1740
ttaaatggca aagataatat aaaagctgca gcccactgcg cgacaaggct gcgcttagtt   1800
atcaatgatg aatcaaaaat agaccaaaaa gcattggatg cgcatccgga tgtaaaaggt   1860
acatttaaaa caaacggcca gtaccaaatt attataggac cggggatgt cgataaagtt   1920 tatgctgaat tgatcaaatt aaccggcctt ccggatatga caacgagga tgtgaaaaaa   1980 acttcgaatg aaaagcaggg aaatgtatta ttaagattaa tcaaggtatt atctgatatt   2040
tttgttccaa ttattcctgc acttgttgcc ggcggtttgc tgatggcttt aaacaatgta   2100
ttgacagcgg aacacctatt cacaaagaag gcaatagtgg aattgtaccc gggactgaaa   2160
gatatagcgt catttatcaa taccatgtcg gctgccccat ttactttctt gccggtttta   2220
atcggatatt ccgcaaccaa acggtttggt gggaatccgt atttaggagc tgctatgggg   2280
atgatcatgt tatctcctgc attgacaagc gggtatgatg ttgttagcgc aaaagcatca   2340
ggggagttgg cttattggca tatttttgga ttaaaagtcg cgcaggccgg ttaccaaggc   2400
tctgtcttgc cggtattggt agtttcatgg attttagcta aattagagaa attttttccat  2460 aaatatattt caaatgcatt tgattttacg ttcacaccga tgcttgccat tatcattaca   2520
ggatttctaa cgtttacatt tgttgggcct gttatgcgtg atgtgagtga tgggttaacc   2580
aatggaatta tgtggttata taatgcaaca ggcgcggttg gaactgcaat cttggactg    2640 ttttattcac cgattgtcat taccggtctg catcaaagtt ttcctgcaat tgaaaccaca   2700
cttttggctg atattgcaaa aaccggcgga tcgtttgtat taccaatcgc ctctatggct   2760
aatattgcgc aaggtgctgc ttgtcttgcc gtattcttta ttacaaaaag taaaaaacaa   2820
aaaagcttat cttcttcagc aagtatttca gctctttgg ggattacaga accggctatt    2880
ttcgggatta acttgaaatt aaggtatccg ttctttttgtg caatggttgc ttccggtatt   2940
gcttctatat ttattggcat gttccatgtg ttatcagttt caatgggacc tgcaagtgta   3000 attggttta tttgcattcg ctcacaatct atccttgcct ttgtcatgag tggcgcaata    3060
agttttgtta tcgccttcac aacaacgtat atatatggaa gacgggcggc ggcaaaggaa   3120
```

-continued

```
caaaatacga ttacgaatga acgggtatct ggaaaagaac aaataggaga aacggctgct   3180
tcggctacgg cccctgctgg taatatcatc atttttgccc cggttgaagg tgaaacaatg   3240
agcttaaaaa atgtgaagga taaattattt tcatctgaat taatgggtaa aggggcagcc   3300
atcatgccga aaaacggcga tgtctatgct ccttgtgacg gaattttgac cacggtattt   3360
gatacacatc atgcatacgg cattaaaacg gaagatggag cagaaatttt aattcacatt   3420
ggtattgaca cggttaatct gaaaggcgaa tattttacaa gttacgtaga aaaaggtcag   3480
acggtaaacc aaggcgacaa actatgcagt tttgatctgg agaaaattaa agaacttggt   3540
tatgatccaa ccgtgatcac cgtcgtgacc aacacagcag attatgcggc tgttgaagga   3600
tttaatcatg atcatgataa ggtaaaacag gggagccagt tcatcacttt aacaccgaaa   3660
gctactcttt aagcatgc                                                3678
```

```
<210> SEQ ID NO 6
<211> LENGTH: 40
<212> TYPE: DNA
<213> ORGANISM: Artificial
<220> FEATURE:
<223> OTHER INFORMATION: Synthetic primer

<400> SEQUENCE: 6
agtactgcat gcttaaagag tagctttcgg tgttaaagtg                            40

<210> SEQ ID NO 7
<211> LENGTH: 48
<212> TYPE: DNA
<213> ORGANISM: Artificial
<220> FEATURE:
<223> OTHER INFORMATION: Synthetic primer

<400> SEQUENCE: 7
agtactgagc tcctatttat taatagaatg aagactccag tagttccc                   48

<210> SEQ ID NO 8
<211> LENGTH: 36
<212> TYPE: DNA
<213> ORGANISM: Artificial
<220> FEATURE:
<223> OTHER INFORMATION: Synthetic primer

<400> SEQUENCE: 8
cgcgtcgact gtggataaga caacaggatt cgtatg                                36

<210> SEQ ID NO 9
<211> LENGTH: 53
<212> TYPE: DNA
<213> ORGANISM: Artificial
<220> FEATURE:
<223> OTHER INFORMATION: Synthetic primer

<400> SEQUENCE: 9
ctaaatcaat tttattaaag tccatgggtc caccccgttc ttttcttttt gtg             53

<210> SEQ ID NO 10
<211> LENGTH: 53
<212> TYPE: DNA
<213> ORGANISM: Artificial
<220> FEATURE:
<223> OTHER INFORMATION: Synthetic primer

<400> SEQUENCE: 10
cacaaaaaga aaagaacggg gtggacccat ggactttaat aaaattgatt tag             53
```

```
<210> SEQ ID NO 11
<211> LENGTH: 27
<212> TYPE: DNA
<213> ORGANISM: Artificial
<220> FEATURE:
<223> OTHER INFORMATION: Synthetic primer

<400> SEQUENCE: 11
cgcagatctc cttcttcaac taacggg                                            27

<210> SEQ ID NO 12
<211> LENGTH: 71
<212> TYPE: DNA
<213> ORGANISM: Artificial
<220> FEATURE:
<223> OTHER INFORMATION: Synthetic primer

<400> SEQUENCE: 12
cccgtcgacg ctagctaccg ttcgtataat gtatgctata cgaagttatg tggataagac        60
aacaggattc g                                                             71

<210> SEQ ID NO 13
<211> LENGTH: 70
<212> TYPE: DNA
<213> ORGANISM: Artificial
<220> FEATURE:
<223> OTHER INFORMATION: Synthetic primer

<400> SEQUENCE: 13
cgcagatctt accgttcgta tagcatacat tatacgaagt tatccttctt caactaacgg        60
ggcaggttag                                                               70

<210> SEQ ID NO 14
<211> LENGTH: 34
<212> TYPE: DNA
<213> ORGANISM: Artificial
<220> FEATURE:
<223> OTHER INFORMATION: Synthetic primer

<400> SEQUENCE: 14
cgcctcgaga gatctggccg ggctttatgg gagg                                    34

<210> SEQ ID NO 15
<211> LENGTH: 37
<212> TYPE: DNA
<213> ORGANISM: Artificial
<220> FEATURE:
<223> OTHER INFORMATION: Synthetic primer

<400> SEQUENCE: 15
gccgagctcg catgcccctg atcaaccggg tcagtgc                                 37

<210> SEQ ID NO 16
<211> LENGTH: 33
<212> TYPE: DNA
<213> ORGANISM: Artificial
<220> FEATURE:
<223> OTHER INFORMATION: Synthetic primer

<400> SEQUENCE: 16
cccgctagcc gtttcaatca catagtcgta ttg                                     33

<210> SEQ ID NO 17
<211> LENGTH: 37
<212> TYPE: DNA
```

```
<213> ORGANISM: Artificial
<220> FEATURE:
<223> OTHER INFORMATION: Synthetic primer

<400> SEQUENCE: 17
ccggtcgacg gccttcatgt gcttttgccg caaattc                            37

<210> SEQ ID NO 18
<211> LENGTH: 1146
<212> TYPE: DNA
<213> ORGANISM: Artificial
<220> FEATURE:
<223> OTHER INFORMATION: CAT construct

<400> SEQUENCE: 18
gtcgactgtg gataagacaa caggattcgt atgccctttt ttgtataaag caggcaaaac     60
agagcattaa atgcaggaaa atcgcagaag atcataccta aaaatgaaaa tgtggtaaat    120
ttttagagta aattttttta atctaatcta gaaaatcagt acatcgcaaa aagctcgggt    180
tttaagtatg ttttgcttca ggcggtaaaa cttcgtataa taagggagag gcctatccta    240
ttataaaagc cgctttcggc attttgcctt gggagccggc cccggtttag acgggacgta    300
cagccgtttc accggctaac caggccccctt tttggaagcg aagatccgga aatcaagatc    360
agctgtatag atatcaattt ttggaacaca aaaagaaaag aacggggtgg acccatggac    420
tttaataaaa ttgatttaga caattggaag agaaaagaga tatttaatca ttatttgaac    480
caacaaacga cttttagtat aaccacagaa attgatatta gtgttttata ccgaaacata    540
aaacaagaag gatataaatt ttaccctgca tttatttttct tagtgacaag ggtgataaac    600
tcaaatacag cttttagaac tggttacaat agcgacggag agttaggtta ttgggataag    660
ttagagccac tttatacaat ttttgatggt gtatctaaaa cattctctgg tatttggact    720
cctgtaaaga atgacttcaa agagttttat gatttatacc tttctgatgt agagaaatat    780
aatggttcgg ggaaattgtt tcccaaaaca cctatacctg aaaatgcttt ttctctttct    840
attattccgt ggacttcatt tactgggttt aacttaaata tcaataataa tagtaattac    900
cttctaccca ttattacagc aggaaaattc attaataaag gtaattcaat atatttaccg    960
ctatctttac aggtacatca ttctgtttgt gatggttatc atgcaggatt gtttatgaac   1020
tctattcagg aattgtcaga taggcctaat gactggcttt tataatatga gataatgccg   1080
actgtacttt ttacagtcgg ttttctaatg tcactaacct gccccgttag ttgaagaagg   1140
agatct                                                             1146
```